(12) United States Patent
Hashimoto et al.

(10) Patent No.: US 10,980,606 B2
(45) Date of Patent: Apr. 20, 2021

(54) REMOTE-CONTROL MANIPULATOR SYSTEM AND METHOD OF OPERATING THE SAME

(71) Applicant: KAWASAKI JUKOGYO KABUSHIKI KAISHA, Kobe (JP)

(72) Inventors: Yasuhiko Hashimoto, Kobe (JP); Masayuki Kamon, Akashi (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 303 days.

(21) Appl. No.: 15/755,179

(22) PCT Filed: May 27, 2016

(86) PCT No.: PCT/JP2016/002587
§ 371 (c)(1),
(2) Date: Feb. 26, 2018

(87) PCT Pub. No.: WO2017/033360
PCT Pub. Date: Mar. 2, 2017

(65) Prior Publication Data
US 2018/0257240 A1    Sep. 13, 2018

(30) Foreign Application Priority Data

Aug. 25, 2015    (JP) .............................. JP2015-165479

(51) Int. Cl.
*B25J 13/08*    (2006.01)
*A61B 34/37*    (2016.01)
(Continued)

(52) U.S. Cl.
CPC .............. *A61B 34/37* (2016.02); *A61B 34/32* (2016.02); *B23P 19/04* (2013.01); *B23Q 15/12* (2013.01);
(Continued)

(58) Field of Classification Search
CPC ......... A61B 34/37; A61B 34/32; A61B 34/70; A61B 34/35; G05B 19/4182;
(Continued)

(56) References Cited

U.S. PATENT DOCUMENTS 4,837,734 A    6/1989 Ichikawa et al.
5,706,195 A    1/1998 Corby, Jr. et al.
(Continued)

FOREIGN PATENT DOCUMENTS

JP    S62-199376 A    9/1987
JP    H04-269185 A    9/1992
(Continued)

OTHER PUBLICATIONS

Jul. 19, 2016 International Search Report issued in International Patent Application No. PCT/JP2016/002587.
(Continued)

*Primary Examiner* — Adam R Mott
(74) *Attorney, Agent, or Firm* — Oliff PLC (57) ABSTRACT

A remote-control manipulator system includes a manipulator configured to receive a manipulating instruction from an operator, a slave arm configured to perform a series of works comprised of a plurality of processes, a camera configured to image operation of the slave arm, a display device configured to display an image captured by the camera, a storage device configured to store information related to environment in a workspace as an environment model, and a control device. The control device is configured, while operating the slave arm manually or hybridly, to acquire circumference information that is information related to a circumference area of an area imaged by the camera based on the environment model stored in the storage device, and
(Continued)

display on the display device so that the image captured by the camera and the circumference information are interlocked.

18 Claims, 9 Drawing Sheets

(51) Int. Cl.

| | | |
|---|---|---|
| G05B 19/418 | (2006.01) | |
| B25J 9/00 | (2006.01) | |
| B25J 9/16 | (2006.01) | |
| B23P 19/04 | (2006.01) | |
| B25J 13/00 | (2006.01) | |
| B25J 19/04 | (2006.01) | |
| B25J 3/00 | (2006.01) | |
| B25J 13/06 | (2006.01) | |
| B25J 18/00 | (2006.01) | |
| B25J 19/02 | (2006.01) | |
| B25J 3/04 | (2006.01) | |
| B23Q 15/12 | (2006.01) | |
| B25J 13/02 | (2006.01) | |
| B25J 11/00 | (2006.01) | |
| G06F 3/01 | (2006.01) | |
| H04N 5/232 | (2006.01) | |
| H04N 7/18 | (2006.01) | |
| A61B 34/32 | (2016.01) | |
| G06T 7/62 | (2017.01) | |
| G06T 7/70 | (2017.01) | |
| B23P 21/00 | (2006.01) | |

(52) U.S. Cl.
CPC . *B25J 3/00* (2013.01); *B25J 3/04* (2013.01); *B25J 9/0081* (2013.01); *B25J 9/0084* (2013.01); *B25J 9/0087* (2013.01); *B25J 9/161* (2013.01); *B25J 9/1602* (2013.01); *B25J 9/163* (2013.01); *B25J 9/1612* (2013.01); *B25J 9/1628* (2013.01); *B25J 9/1633* (2013.01); *B25J 9/1638* (2013.01); *B25J 9/1641* (2013.01); *B25J 9/1646* (2013.01); *B25J 9/1653* (2013.01); *B25J 9/1664* (2013.01); *B25J 9/1669* (2013.01); *B25J 9/1674* (2013.01); *B25J 9/1682* (2013.01); *B25J 9/1689* (2013.01); *B25J 9/1697* (2013.01); *B25J 11/008* (2013.01); *B25J 13/00* (2013.01); *B25J 13/003* (2013.01); *B25J 13/006* (2013.01); *B25J 13/02* (2013.01); *B25J 13/025* (2013.01); *B25J 13/06* (2013.01); *B25J 13/065* (2013.01); *B25J 13/08* (2013.01); *B25J 13/084* (2013.01); *B25J 13/085* (2013.01); *B25J 13/087* (2013.01); *B25J 13/088* (2013.01); *B25J 18/00* (2013.01); *B25J 19/023* (2013.01); *B25J 19/028* (2013.01); *B25J 19/04* (2013.01); *G05B 19/4182* (2013.01); *G06F 3/017* (2013.01); *G06T 7/62* (2017.01); *G06T 7/70* (2017.01); *H04N 5/23219* (2013.01); *H04N 7/181* (2013.01); *B23P 21/00* (2013.01); *B23P 21/002* (2013.01); *G05B 2219/33007* (2013.01); *G05B 2219/35464* (2013.01); *G05B 2219/37297* (2013.01); *G05B 2219/39004* (2013.01); *G05B 2219/39102* (2013.01); *G05B 2219/39439* (2013.01); *G05B 2219/39531* (2013.01); *G05B 2219/39533* (2013.01); *G05B 2219/40022* (2013.01); *G05B 2219/40134* (2013.01); *G05B 2219/40136* (2013.01); *G05B 2219/40139* (2013.01); *G05B 2219/40142* (2013.01); *G05B 2219/40143* (2013.01); *G05B 2219/40145* (2013.01); *G05B 2219/40146* (2013.01); *G05B 2219/40161* (2013.01); *G05B 2219/40162* (2013.01); *G05B 2219/40163* (2013.01); *G05B 2219/40169* (2013.01); *G05B 2219/40182* (2013.01); *G05B 2219/40183* (2013.01); *G05B 2219/40195* (2013.01); *G05B 2219/40387* (2013.01); *G05B 2219/40627* (2013.01); *Y10S 901/02* (2013.01); *Y10S 901/03* (2013.01); *Y10S 901/08* (2013.01); *Y10S 901/09* (2013.01); *Y10S 901/10* (2013.01); *Y10S 901/27* (2013.01); *Y10S 901/41* (2013.01); *Y10S 901/46* (2013.01); *Y10S 901/47* (2013.01)

(58) Field of Classification Search
CPC .......... G05B 2219/40136; G05B 2219/40162; G05B 2219/40195; G05B 2219/40134; G05B 2219/40183; G05B 2219/40169; G05B 2219/33007; G05B 2219/40142; G05B 2219/35464; G05B 2219/39533; G05B 2219/40163; G05B 2219/39531; G05B 2219/40022; G05B 2219/39439; G05B 2219/40627; G05B 2219/40146; G05B 2219/40161; G05B 2219/40139; G05B 2219/40387; G05B 2219/40145; G05B 2219/40182; G05B 2219/39004; G05B 2219/40143; G05B 2219/39102; G05B 2219/37297; G05B 2219/40091; G05B 2219/40099; G05B 2219/40167; G05B 2219/40168; B25J 9/1646; B25J 9/0081; B25J 13/087; B25J 13/085; B25J 9/1602; B25J 19/028; B25J 9/1612; B25J 9/1674; B25J 9/1653; B25J 13/084; B25J 13/025; B25J 13/065; B25J 13/003; B25J 11/008; B25J 9/163; B25J 13/02; B25J 9/168; B25J 9/1633; B25J 3/04; B25J 19/023; B25J 9/1689; B25J 9/1682; B25J 9/1664; B25J 9/161; B25J 18/00; B25J 13/088; B25J 13/06; B25J 9/1669; B25J 9/1697; B25J 9/0084; B25J 19/04; B25J 13/00; B25J 9/126; B25J 19/06; B25J 19/02; B25J 11/005; B25J 9/1692; B25J 9/1661; B25J 9/1666; B25J 9/1671; B25J 9/1676; B25J 13/04; B25J 13/08; B25J 13/006; G06T 7/70; G06T 7/62; G06T 7/75; H04N 7/181; H04N 5/23219; G06F 3/017; B23Q 15/12; B23P 21/002; B23P 21/00; Y10S 901/02; Y10S 901/46; Y10S 901/10; Y10S 901/41; Y10S 901/27; Y10S 901/03; Y10S 901/08; Y10S 901/47; Y10S 901/09
See application file for complete search history.

(56) References Cited

U.S. PATENT DOCUMENTS

| | | | |
|---|---|---|---|
| 5,745,387 A | | 4/1998 | Corby, Jr. et al. |
| 9,789,608 B2* | | 10/2017 | Itkowitz ............... B25J 9/1689 |
| 2009/0326318 A1* | | 12/2009 | Tognaccini ............ A61B 34/30 |
| | | | 600/104 |

(56) References Cited

U.S. PATENT DOCUMENTS

2011/0311127 A1 12/2011 Mizutani et al.
2015/0157411 A1 6/2015 Choi

FOREIGN PATENT DOCUMENTS

| JP | H09-212219 A | 8/1997 |
|---|---|---|
| JP | 3217383 B2 | 10/2001 |
| JP | 2002-077675 A | 3/2002 |
| JP | 2003-311661 A | 11/2003 |
| JP | 2006-113858 A | 4/2006 |
| JP | 2014-503376 A | 2/2014 |

OTHER PUBLICATIONS

Feb. 27, 2018 International Preliminary Report on Patentability issued in International Patent Application No. PCT/JP2016/002587.

* cited by examiner

REMOTE-CONTROL MANIPULATOR SYSTEM AND METHOD OF OPERATING THE SAME

TECHNICAL FIELD

The present disclosure relates to a remote-control manipulator system and a method of operating the same.

BACKGROUND ART

Master-slave type remote control devices in which operation of the slave arm follows operation of a master arm which is operated by an operator are known (e.g., see Patent Document 1). The remote control device disclosed in Patent Document 1 includes a camera which captures an image of a work environment, an environment model memory means for storing as an environment model, information related to the position and posture etc. of an object which is a target of the work environment by a robot, and a synthesized image generation means for generating a synthesized image which is obtained by synthesizing the image captured by the camera with an image where information related to positioning obtained based on the environment model memory means is graphically indicated. The device is configured, when performing a manual operation of the robot, to be capable of guiding the manual operation, by displaying the synthesized image on a display device.

REFERENCE DOCUMENT OF CONVENTIONAL ART

Patent Document

[Patent Document 1] JP2003-311661A

DESCRIPTION OF THE DISCLOSURE

Problems to be Solved by the Disclosure

However, a remote manipulation device disclosed in Patent Document 1 does not take a circumference situation of the robot (slave arm) currently manipulated by the operator into consideration. Thus, in order to avoid the manipulating robot from contacting other robots etc. or select a moving route of the robot, the operator needs to always watch carefully areas other than an area currently imaged by the camera. Therefore, the worker's burden is large and there is still room for an improvement in terms of an improvement of work efficiency.

The present disclosure is to solve the conventional problems described above, and one purpose thereof is to provide a remote-control manipulator system and a method of operating the same, which reduces a worker's burden and improve work efficiency.

SUMMARY OF THE DISCLOSURE

In order to solve the conventional problem, a remote-control manipulator system according to the present disclosure includes a manipulator configured to receive a manipulating instruction from an operator, a slave arm, installed in a workspace and configured to perform a series of works comprised of a plurality of processes, a camera configured to image operation of the slave arm, a display device configured to display an image captured by the camera, a storage device configured to store information related to environment in the workspace as an environment model, and a control device. The control device is configured, while operating the slave arm manually or hybridly, to acquire circumference information that is information related to a circumference area of an area imaged by the camera based on the environment model stored in the storage device, and display on the display device so that the image captured by the camera and the circumference information are interlocked.

Thus, since the circumference information of the slave arm is also displayed on the display device in addition to the area imaged by the camera, the operator becomes easier to grasp the situation of the slave arm. Therefore, a worker's burden is reduced and work efficiency is improved.

Further, a method of operating a remote-control manipulator system according to the present disclosure is a method of operating a remote-control manipulator system including a manipulator configured to receive a manipulating instruction from an operator, a slave arm installed in a workspace and configured to perform a series of works comprised of a plurality of processes, a camera configured to image operation of the slave arm, a display device configured to display an image captured by the camera, and a storage device configured to store information related to environment in the workspace as an environment model. The method includes (A) while the slave arm is operated manually or hybridly, identifying circumference information that is information related to a circumference area of an area imaged by the camera based on the environment model stored in the storage device, and (B) causing the display device to display so that the image captured by the camera and the circumference information are interlocked.

Thus, since the circumference information of the slave arm is also displayed on the display device in addition to the area imaged by the camera, the operator becomes easier to grasp the situation of the slave arm. Therefore, the worker's burden is reduced and the work efficiency is improved.

Effect of the Disclosure

According to the remote-control manipulator system of the present disclosure and method of operating the same, the worker's burden is reduced and the work efficiency is improved.

MODES FOR CARRYING OUT THE DISCLOSURE

Hereinafter, embodiments of the present disclosure will be described with reference to the drawings. Note that, throughout the drawings, the same reference characters are given to the same or corresponding parts to omit redundant description. Moreover, throughout the drawings, some elements for describing the present disclosure are extracted and illustrated, and illustration of other elements may be omitted. Further, the present disclosure is not limited to the following embodiments.

Embodiment 1

A remote-control manipulator system according to Embodiment 1 includes a manipulator which receives a manipulating instruction from an operator, a slave arm which is installed in a workspace and performs a series of works comprised of a plurality of processes, a camera which images operation of the slave arm, a display device which displays the image captured by the camera, a storage device which stores information related to environment in the workspace as an environment model, and a control device. The system is configured so that, when the slave arm is in a manual operation or a hybrid operation, the control device acquires based on the environment model stored in the storage device, circumference information which is information related to a circumference area of an area imaged by the camera, and displays on the display device so that the image captured by the camera and the circumference information are interlocked.

Moreover, in the remote-control manipulator system according to Embodiment 1, the display device may be configured to display the image captured by the camera in a center portion and display the circumference information in a circumferential edge portion.

Moreover, in the remote-control manipulator system according to Embodiment 1, the control device may be configured to acquire posture information on the slave arm, identify an imaging position of the camera based on the posture information, and identify the circumference information based on the environment model.

Further, in the remote-control manipulator system according to Embodiment 1, the circumference information may be an operating area of the slave arm.

Below, one example of the remote-control manipulator system according to Embodiment 1 is described with reference to FIGS. 1 to 6.

[Configuration of Remote-Control Manipulator System]

Figure 1:
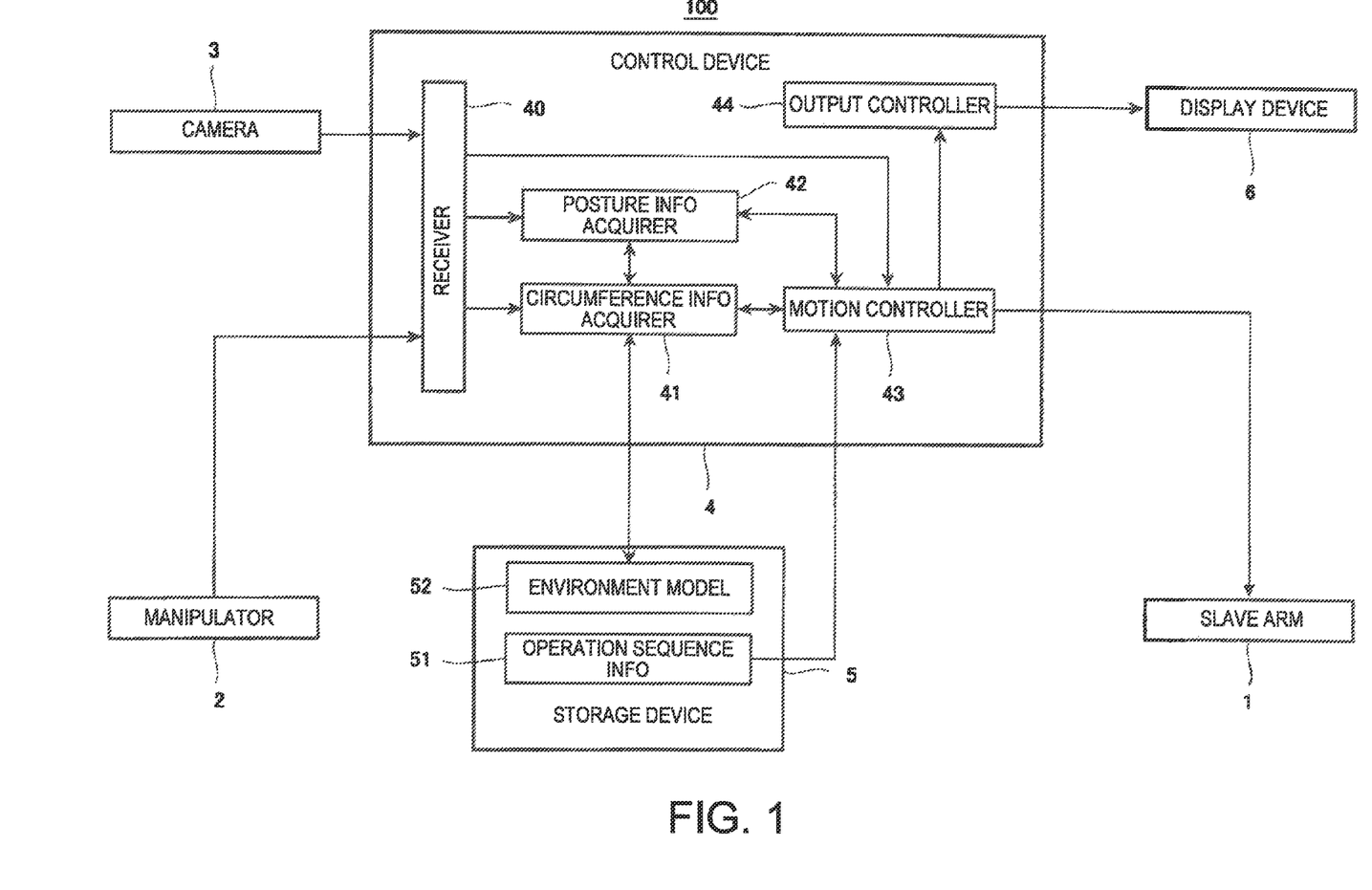
FIG. 1 is a block diagram illustrating an outline configuration of a remote-control manipulator system according to Embodiment 1.

FIG. 1 is a block diagram illustrating an outline configuration of the remote-control manipulator system according to Embodiment 1.

As illustrated in FIG. 1, the remote-control manipulator system 100 according to Embodiment 1 includes a slave arm 1, a manipulator 2, a camera 3, a control device 4, a storage device 5, and a display device 6, and it is configured so that the slave arm 1 is operated by an operator manipulating the manipulator 2.

The slave arm 1 is a robot which is installed in a workspace and performs a series of works comprised of a plurality of processes. Note that the series of works comprised of the plurality of processes may include works, such as assembling of component(s) to a product and painting.

The slave arm 1 according to Embodiment 1 is an articulated robot, in a line production or a cell production, which is utilized at a manufacturing plant where products are produced by assembling electric and/or electronic components etc., is disposed along a workbench provided to the manufacturing plant, and is capable of performing at least one of works, such as transferring, assembling or relocating of component(s), and converting the posture, to workpiece(s) on the workbench. Note that the embodiment of the slave arm 1 is not limited to the configuration described above, but may be widely applied to any articulated robots, regardless of a horizontal articulated type or a vertical articulated type.

Here, the configuration of the slave arm 1 is described with reference to FIG. 2.

Figure 2:
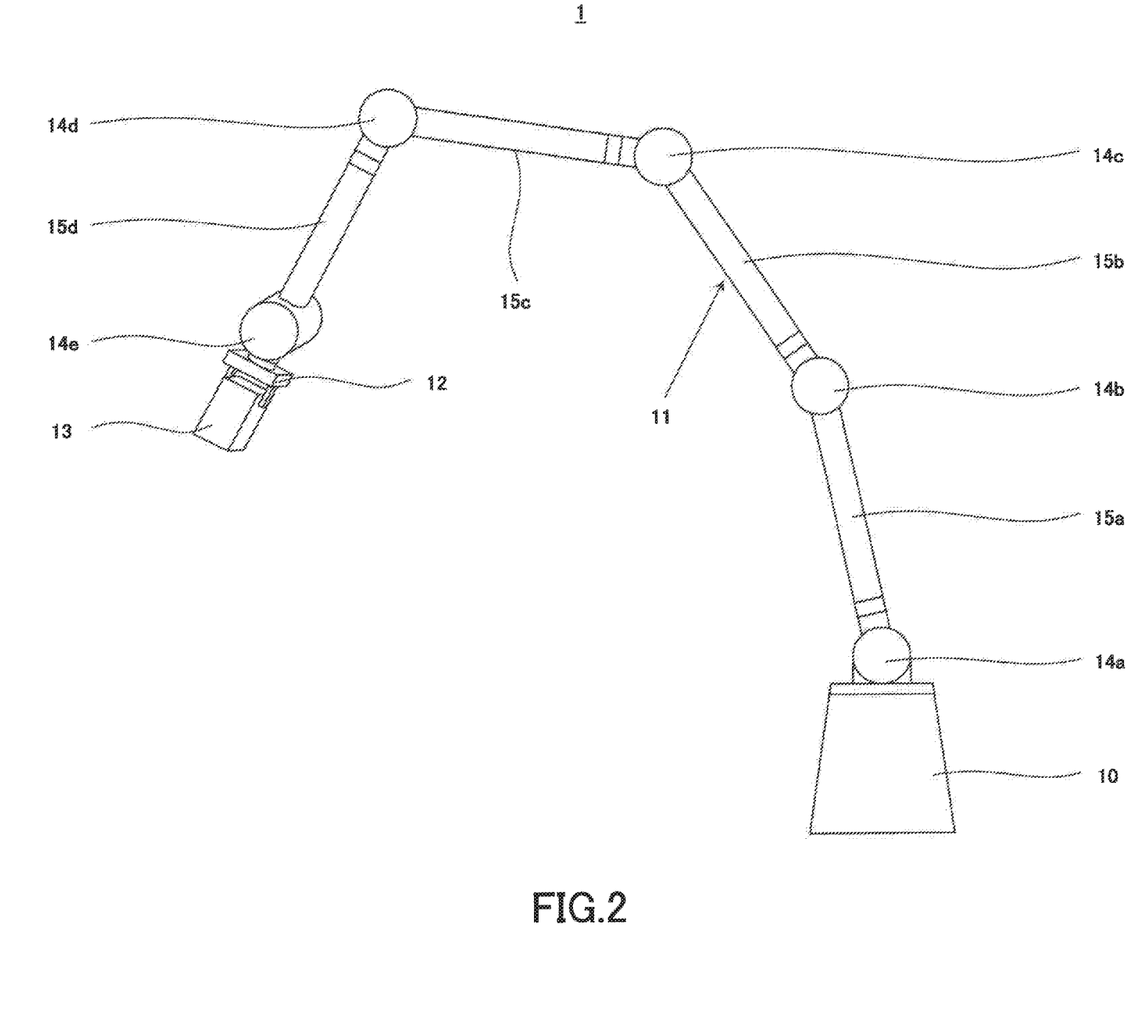
FIG. 2 is a schematic diagram illustrating an outline configuration of the slave arm in the remote-control manipulator system illustrated in FIG. 1.

FIG. 2 is a schematic diagram illustrating an outline configuration of the slave arm in the remote-control manipulator system illustrated in FIG. 1.

As illustrated in FIG. 2, the slave arm 1 includes a base 10, a base shaft part 11, and a tip-end part 12, and is configured by various kinds of end effectors attached to the tip-end part 12 to execute various works. Note that, in Embodiment 1, although a form in which a hand part for gripping a target object 13 is attached to the tip-end part 12 is adopted, it is not be limited to this configuration but an end effector, such as a welder for welding to the target object, may be attached.

The base 10 is a foundation for installing the slave arm 1 on the ground, an installation table or the like. The base shaft part 11 is provided on an upper surface of the base 10. The base shaft part 11 is a part which defines a main operational posture of the slave arm 1, and is comprised of a plurality of joint parts 14a-14e, and link parts 15a-15d which connect the respective joint parts.

The joint part 14a joins a tip-end part of the base 10 to a base-end part of the link part 15a, and is configured so that the link part 15a is rotatable about a rotational axis extending vertically, about a rotational axis extending horizontally, and about a rotational axis extending in the extending directions of the link part 15a.

Similarly, the joint part 14b joins a tip-end part of the link part 15a to a base-end part of the link part 15b, and is configured so that the link part 15b is rotatable about a rotational axis extending in the extending directions of the link part 15b, and about a rotational axis extending in directions perpendicular to the rotational axis extending in the extending directions of the link part 15b.

The joint part 14c joins a tip-end part of the link part 15b to a base-end part of the link part 15c, and is configured so that the link part 15c is rotatable about a rotational axis extending in the extending directions of the link part 15c, and about a rotational axis extending in directions perpendicular to the rotational axis extending in the extending directions of the link part 15c.

The joint part 14d joins a tip-end part of the link part 15c to a base-end part of the link part 15d, and is configured so that the link part 15d is rotatable about a rotational axis extending in the extending directions of the link part 15d, and about a rotational axis extending in directions perpendicular to the rotational axis extending in the extending directions of the link part 15d.

The joint part 14e joins a tip-end part of the link part 15d to the tip-end part 12, and is configured so that the tip-end part 12 is rotatable about a rotational axis extending in the extending directions of the tip-end part 12, and about a rotational axis extending in directions perpendicular to the rotational axis extending in the extending directions of the tip-end part 12.

The tip-end part 12 is a part which controls fine positioning of the end effector which performs the work. That is, the slave arm 1 according to Embodiment 1 is configured to define a main posture by the base shaft part 11, and perform the fine positioning corresponding to a work position of the end effector by the tip-end part 12.

In the slave arm 1, a drive motor (not illustrated) provided to each of the joint parts 14a-14e joins the adjacent link parts so as to rotate relatively to each other. Thus, the control device 4 is capable of controlling an angle of each of the joint parts 14a-14e which is rotated by the drive motor, according to manipulating instruction information on the slave arm 1 outputted from the manipulator 2, or operational information defined in an operation sequence information 51 of the storage device 5 described later, to determine a tip-end part position of the slave arm 1.

Note that, the configuration of the slave arm 1 described above is one example, and is not limited to this configuration. The configuration may suitably be changed according to the contents of work which is carried out using the slave arm 1, the workspace, etc.

The manipulator 2 is a device which is installed outside the workspace and receives the manipulating instruction from the operator. The manipulator 2 may be, for example, a master arm, a joystick, or a tablet computer. Note that the manipulator 2 may be separately provided with an input part etc. which inputs a start instruction of the work described later, a notice of completion of the work by the manipulating operation (manual operation), etc. Moreover, the manipulator 2 may be installed in the workspace.

The camera 3 images the slave arm 1 in the workspace as an image. For example, it records as the image, the position or posture of the slave arm 1 in the workspace, a spatial relationship between the slave arm 1 and the workpiece, or a spatial relationship between the slave arm 1 and the assembled component to which the workpiece is attached.

The camera 3 may be disposed at slave arm 1 itself, or may be disposed at a proper place in the workspace. Moreover, the number of cameras 3 disposed may be one or may be plural. The attaching position(s) and the attaching number are arbitrary, as long as the suitable number of cameras 3 is disposed at positions where status information is appropriately acquirable.

The storage device 5 is a readable and writable recording medium, which stores the operation sequence information 51 and the environment model 52 of the remote-control manipulator system 100. Note that, in the remote-control manipulator system 100 according to Embodiment 1, although the storage device 5 is provided separately from the control device 4, but may be integrally provided with the control device 4.

The operation sequence information 51 is information related to an operation sequence which defines the series of works to be performed by the slave arm 1 in the workspace, and includes a program for causing the slave arm 1 to perform an automatic operation. Specifically, it is information where an operation order, an operating mode of the slave arm 1, and an operation flow of the operating mode are associated with each other.

The environment model 52 is information containing names, shapes, disposed positions (coordinates), postures and the like, of the slave arm 1 disposed in the workspace, each apparatus such as a belt conveyor, the target object 13 such as the workpiece etc., the assembled object to which the workpiece is assembled, etc. Specifically, for example, it is information, such as the position or posture of the slave arm 1 in the workspace, the spatial relationship between the slave arm 1 and the workpiece, or the spatial relationship between the slave arm 1 and the assembled component to which the workpiece is assembled.

The control device 4 controls the operation of the slave arm 1, and includes a receiver 40, a circumference information acquirer 41, a posture information acquirer 42, a motion controller 43, and an output controller 44, as functional blocks. The control device 4 may be comprised of, for example, an arithmetic part (not illustrated), such as a microcontroller, an MPU and a PLC (Programmable Logic Controller), a logic circuit, etc., and a memory part (not illustrated), such as a ROM or a RAM. Moreover, each functional block provided to the control device 4 is implementable by the arithmetic part of the control device 4 reading and executing the program stored in the memory part or the storage device 5. Note that the control device 4 may not only be in a form comprised of a single control device, but also in a form comprised of a group of control devices in which a plurality of control devices collaborate with each other to execute the control of the slave arm 1 (remote-control manipulator system 100).

The receiver 40 receives an input signal transmitted from the outside of the control device 4. The input signal received by the receiver 40 may be, for example, a signal transmitted from the manipulator 2, a signal transmitted from a manipulating instruction part (not illustrated) other than the manipulator 2, etc.

The circumference information acquirer 41 acquires modeled (simulated) circumference information which is information related to the circumference area of the area currently imaged by the camera 3, based on each information on the environment model 52 stored in the storage device 5, the image information received from the camera 3 by the receiver 40, the posture information on the slave arm 1 acquired from the posture information acquirer 42.

Note that, the modeling of the circumference information may suitably be executed by using known technologies. Moreover, the circumference information may be posture information on the entire link parts 15a-15d of the slave arm 1, or may be information on each apparatus disposed in an operating range of the slave arm 1, or may be information on each apparatus in a work lane where the slave arm 1 is installed. Further, the circumference information may be a computer graphic or may be a deformed figure or illustration.

The posture information acquirer 42 acquires from the motion controller 43 rotation angles of the drive motors provided to the respective joint parts 14a-14e of the slave arm 1, or if position sensors are disposed at the respective link parts 15a-15d of the slave arm 1, acquires posture information on the slave arm 1 currently manipulated by the operator by receiving positional information from the position sensors.

When the receiver 40 receives the manipulating instruction from the manipulator 2 as the input signal, the motion controller 43 determines the operating mode of the process which the slave arm 1 carries out in the series of works by using the manipulating instruction as a trigger. The motion controller 43 is capable of performing the determination of the operating mode of the process which the slave arm 1 carries out next, with reference to the operation sequence information 51 stored in the storage device 5. Once the motion controller 43 determines whether the operating mode is any one of an automatic operation mode, a manual operation mode, and a hybrid operation mode, it controls the slave arm 1 so that the slave arm 1 is operated in the determined operating mode.

Here, the automatic operation mode means that the slave arm 1 operates automatically according to the preset program. Moreover, the manual operation mode means that the slave arm 1 operates according to the manipulating instruction received from the manipulator 2, but the slave arm 1 may operate so as to completely follow the manipulating instruction received from the manipulator 2, or the slave arm 1 may operate while correcting the manipulating instruction received from the manipulator 2 by the preset program (e.g., a hand-shaking correction). Further, the hybrid operation mode means that the operation of the slave arm under operation by the automatic operation is corrected by the manual operation.

If the motion controller 43 determines that the slave arm 1 is to be automatically operated, it reads the operation sequence information 51, and controls the slave arm 1 to carry out the operation defined by the program contained in the operation sequence information 51.

Moreover, if the motion controller 43 determines that the slave arm 1 is to be manually operated, it controls the slave arm 1 to be operated based on the manipulating instruction which the receiver 40 received from the manipulator 2.

Further, if the motion controller 43 determines that the slave arm 1 is hybridly operated, it reads the operation sequence information 51, and causes the slave arm 1 to carry out operation defined by the program contained in the operation sequence information 51. When the receiver 40 receives a correction instructing signal from the manipulator 2 as the input signal while the slave arm 1 is operating automatically, the operation of the slave arm 1 by the automatic operation is corrected to operation according to the correction instructing signal from the manipulator 2.

Then, when the output of the correction instructing signal from the manipulator 2 is stopped and the receiver 40 stops the reception of the correction instructing signal, or when the receiver 40 receives a signal which instructs a resumption of the automatic operation of the slave arm 1 from the manipulator 2, the motion controller 43 resumes the automatic operation of the slave arm 1.

Moreover, while the slave arm 1 is operating in the manual operation mode or the hybrid operation mode, when the operator operates the manipulator 2 to zoom-up or zoom-in a photographic subject which is imaged by the camera 3 (when zoom-up or zoom-in information is acquired from the manipulator 2 through the receiver 40), the motion controller 43 acquires the circumference information from the posture information acquirer 42, and outputs to the output controller 44 the image information and the circumference information which are imaged by the camera 3 and received through the receiver 40.

The output controller 44 controls the display device 6 to output information to be notified to the operator etc. as the image information. The output controller 44 outputs to the display device 6 the image information and the circumference information which are imaged by the camera 3 and inputted from the motion controller 43.

The display device 6 is provided at a position where the operator of the manipulator 2 is able to sense the outputted information (outside of the workspace; and a space where the manipulator 2 is installed), and is to display the information transmitted from the control device 4. For example, the display device 6 may be comprised of a monitor, or if the manipulator 2 is comprised of a tablet computer, the display device 6 may be the tablet computer.

[Operation and Effect of Remote-Control Manipulator System]

Next, operation and effect of the remote-control manipulator system 100 according to Embodiment 1 are described with reference to FIGS. 1 to 7. Note that since the operation of performing the series of works by the operator manipulating the manipulator 2 to operate the slave arm 1 is executed similar to a known remote-control manipulator system, detailed description thereof is omitted. Moreover, the following operation is executed by the arithmetic part of the control device 4 reading the program stored in the memory part or the storage device 5.

Figure 3:
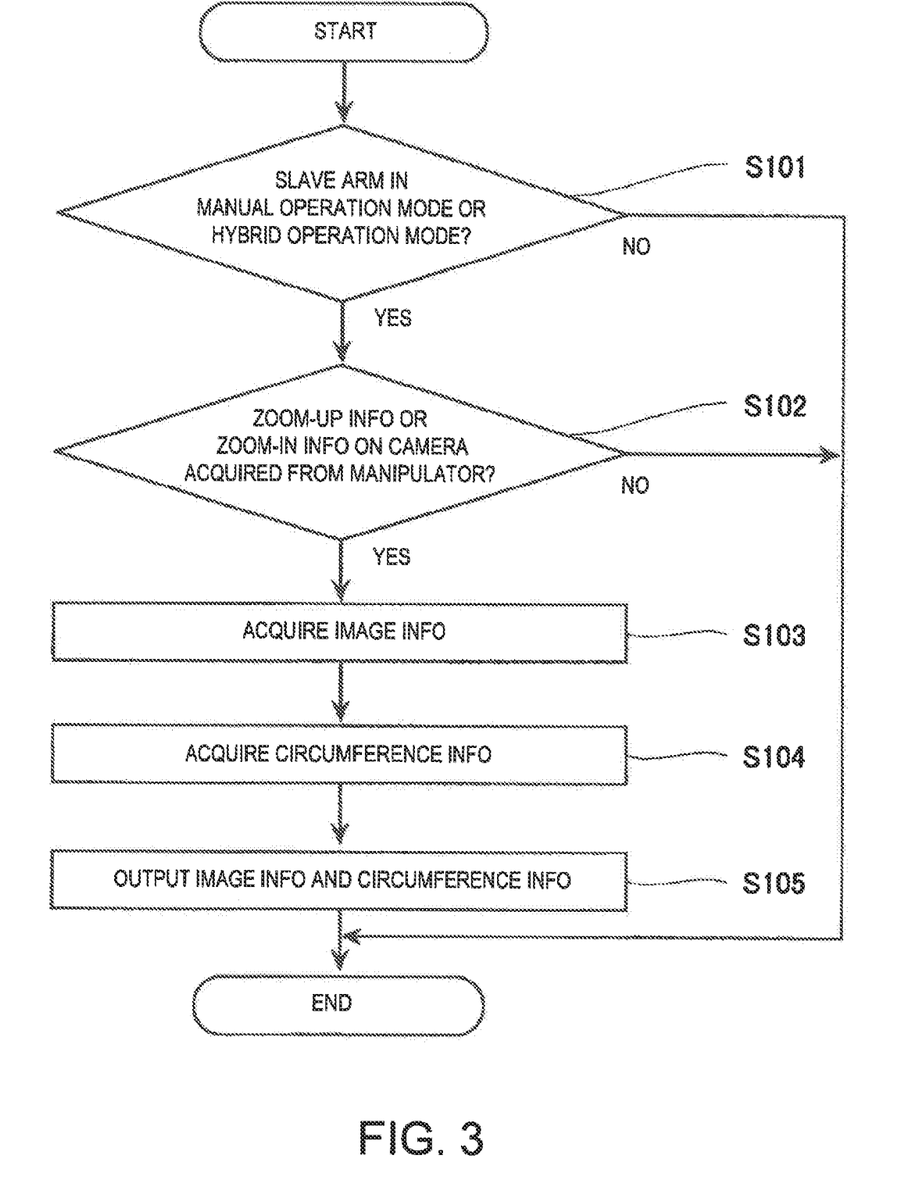
FIG. 3 is a flowchart illustrating operation of the remote-control manipulator system according to Embodiment 1.

FIG. 3 is a flowchart illustrating operation of the remote-control manipulator system according to Embodiment 1. FIGS. 4 to 7 are schematic diagrams illustrating a display screen of the display device in the remote-control manipulator system illustrated in FIG. 1.

Figure 4:
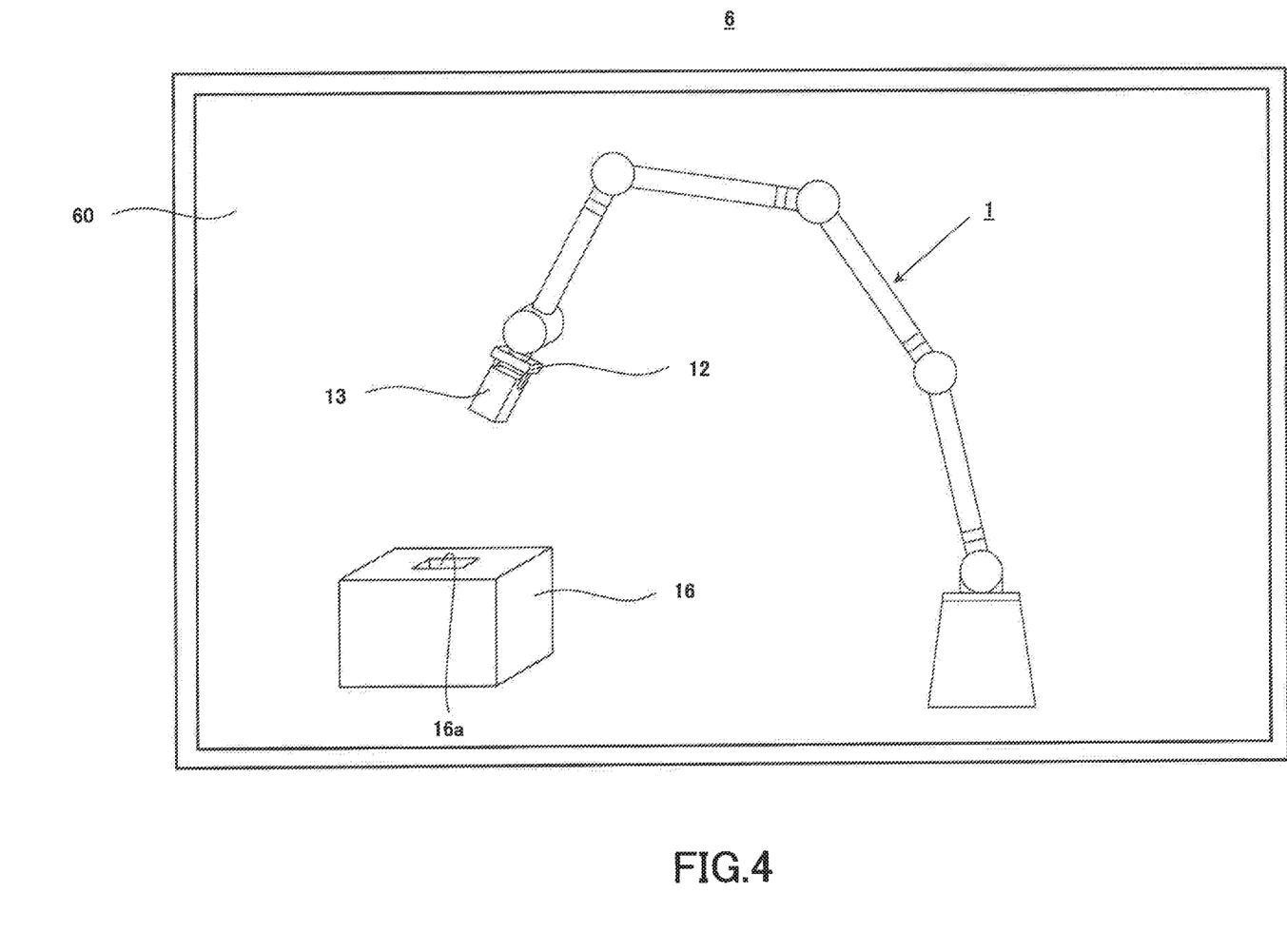
FIG. 4 is a schematic diagram illustrating a display screen of a display device in the remote-control manipulator system illustrated in FIG. 1.

First, as illustrated in FIG. 4, it is assumed that the tip-end part 12 of the slave arm 1 grips a target object 13, a work to insert the target object 13 into a hole 16a of an object 16 is performed, the camera 3 in a state of zoom-back or zoom-out, the slave arm 1 and the object 16 are imaged, and the captured image is displayed on a display screen 60 of the display device 6. Then, as illustrated in FIG. 5, it is assumed that the operator manipulates the manipulator 2 to zoom-up or zoom-in the camera 3 so that the camera 3 images near the tip-end part 12 of the slave arm 1.

Figure 5:
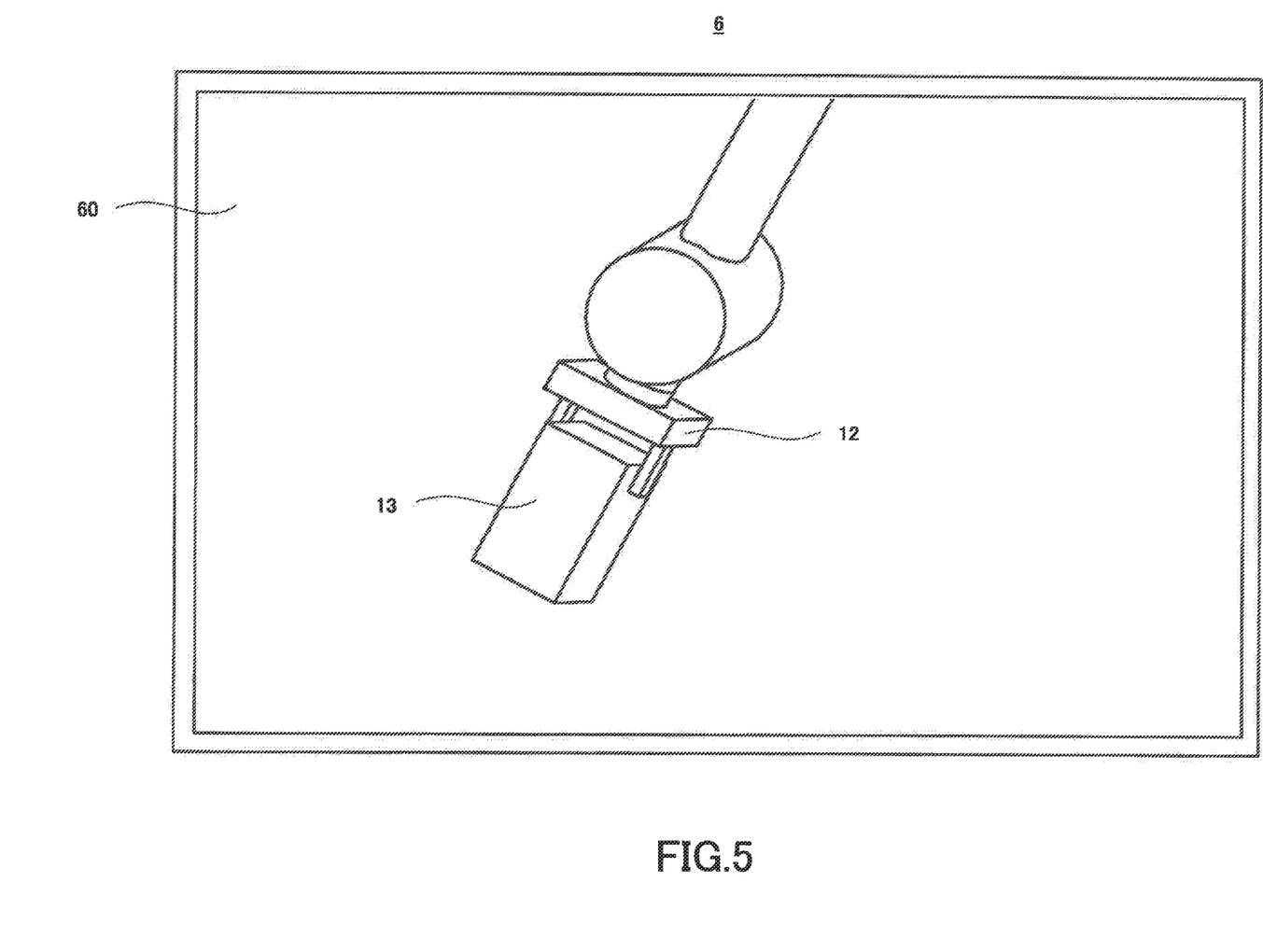
FIG. 5 is a schematic diagram illustrating a display screen of the display device in the remote-control manipulator system illustrated in FIG. 1.

In such a case, in the conventional remote-control manipulator system, as illustrated in FIG. 5, the posture of the entire slave arm 1 is not displayed on the display screen 60 of the display device 6, and a spatial relationship between the slave arm 1 and the object 16 is not displayed, either. Thus, the operator needs to confirm the posture of the slave arm 1, or the spatial relationship between the slave arm 1 and the object 16 by looking at the slave arm 1, etc. or frequently changing the zoom of the camera 3, resulting in a large burden of the worker.

However, in the remote-control manipulator system 100 according to Embodiment 1, the problem of the conventional remote-control manipulator system is eliminated by performing the following operation.

As illustrated in FIG. 3, the control device 4 determines whether the slave arm 1 operates in the manual operation mode or the hybrid operation mode (Step S101). This is because the operator does not need to manipulate the slave arm 1 with the manipulator 2 if the slave arm 1 is executing the automatic operation mode.

Specifically, the motion controller 43 of the control device 4 determines whether the manipulating instruction information on the slave arm 1 is received from the manipulator 2 through the receiver 40, and whether the correction instructing signal is received from the manipulator 2.

If the motion controller 43 of the control device 4 determines that the slave arm 1 is not operated in the manual operation mode or the hybrid operation mode (No at Step S101), it ends this program. Note that, when the control device 4 ends this program, it again executes this program, for example, after 50 msec. On the other hand, if the motion controller 43 of the control device 4 determines that the slave arm 1 is operated in the manual operation mode or the hybrid operation mode (Yes at Step S101), it executes processing illustrated at Step S102.

At Step S102, the motion controller 43 of the control device 4 determines whether zoom-up information or zoom-in information on the camera 3 is acquired from the manipulator 2 through the receiver 40. If the motion controller 43 of the control device 4 determines that the zoom-up information or zoom-in information on the camera 3 is not acquired from the manipulator 2 through the receiver 40 (No at Step S102), it ends this program. Note that, when the control device 4 ends this program, it again executes this program, for example, after 50 msec.

On the other hand, if the motion controller 43 of the control device 4 determines that the zoom-up information or zoom-in information on the camera 3 is acquired from the manipulator 2 through the receiver 40 (Yes at Step S102), it executes processing illustrated at Step S103.

At Step S103, the motion controller 43 of the control device 4 acquires the image information currently imaged by the camera 3 through the receiver 40. Subsequently, the motion controller 43 of the control device 4 acquires the circumference information from the posture information acquirer 42 (Step S104).

Specifically, the posture information acquirer 42 of the control device 4 acquires the rotational speeds etc. of the drive motors provided to the respective joint parts 14a-14e of the slave arm 1 from the motion controller 43 to acquire the posture information on the slave arm 1. Then, the circumference information acquirer 41 of the control device 4 performs the simulation based on each information on the environment model 52 stored in the storage device 5, the image information acquired at Step S103, and the posture information on the slave arm 1 acquired from the posture information acquirer 42 to acquire the circumference information, and outputs it to the motion controller 43. Thus, the motion controller 43 acquires the circumference information.

Next, the motion controller 43 of the control device 4 outputs the image information acquired at Step S103 and the circumference information acquired at Step S104 to the display device 6 through the output controller 44 (Step S105), and ends this program.

Figure 6:
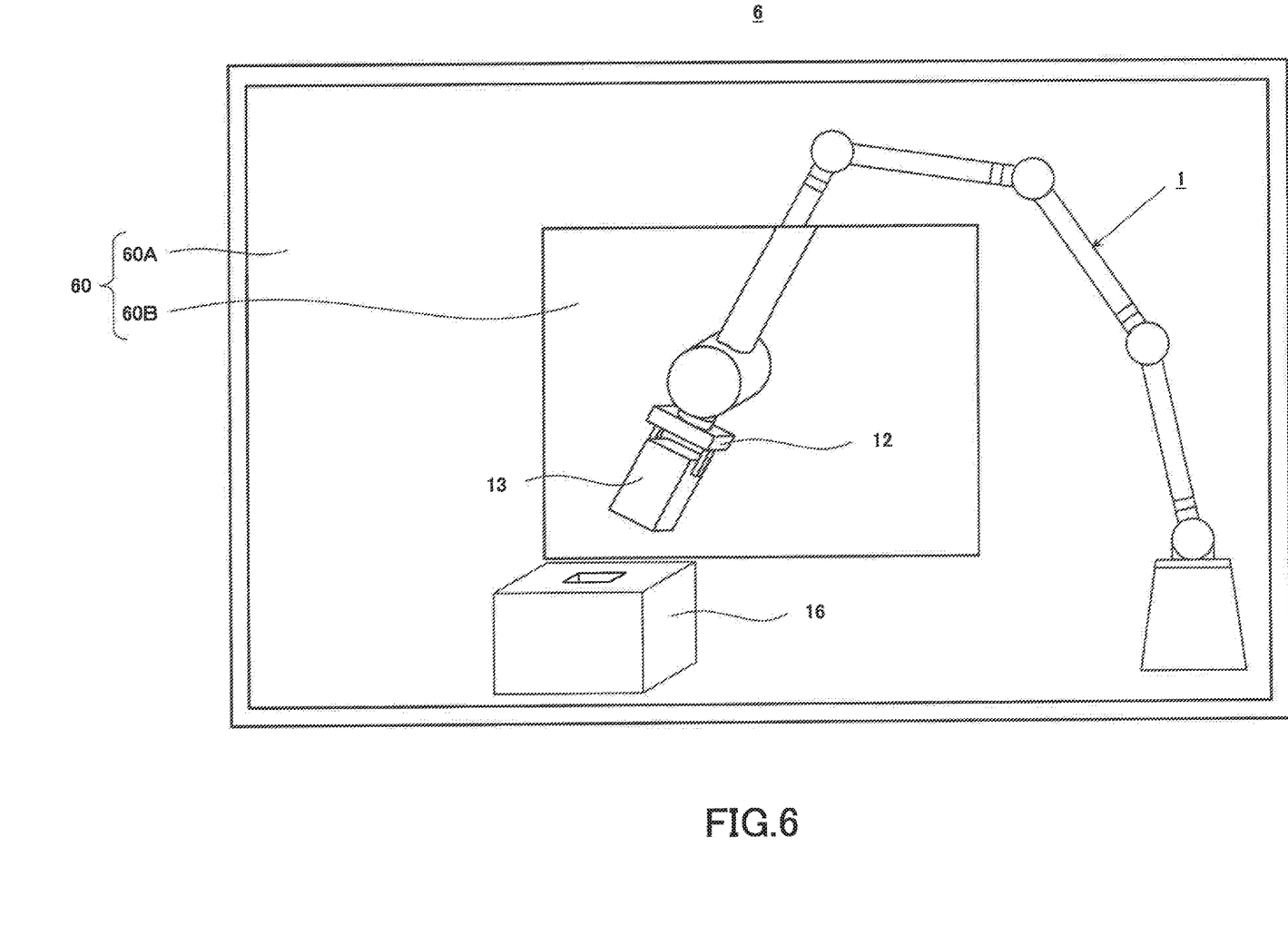
FIG. 6 is a schematic diagram illustrating a display screen of the display device in the remote-control manipulator system illustrated in FIG. 1.

Thus, the display device 6 is capable of displaying on the display screen 60 the image information currently imaged by the camera 3 and the circumference information which is information related to the circumference area of the area currently imaged by the camera 3. Here, as illustrated in FIG. 6, the display device 6 may display, for example, the image information in a center portion 60A of the display screen 60 and the circumference information in a circumferential edge portion 60B of the display screen 60.

Figure 7:
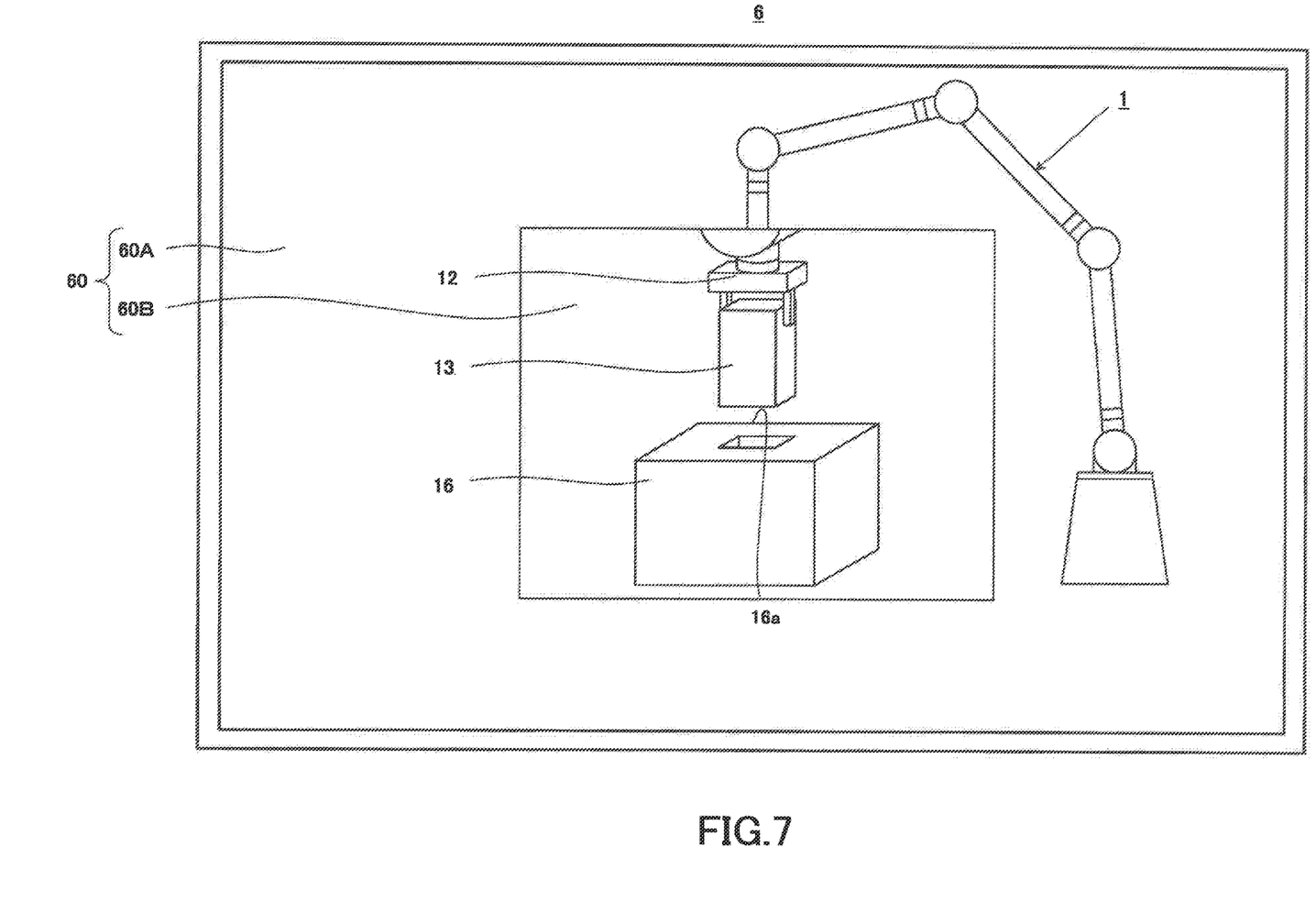
FIG. 7 is a schematic diagram illustrating a display screen of the display device in the remote-control manipulator system illustrated in FIG. 1.

Thus, the display device 6 displays on the display screen 60 the image information currently imaged by the camera 3 and the circumference information which is the information related to the circumference area of the area currently imaged by the camera 3 so that those information are interlocked, thus, the operator is able to grasp the posture of the slave arm 1, or the spatial relationship between the slave arm 1 and the object 16 by looking at the display screen 60 of the display device 6. Therefore, as illustrated in FIG. 7, the operator is able to easily operate the slave arm 1 so that the center axis in the vertical directions of the target object 13 is aligned with the center axis in the vertical directions of the hole 16a of the object 16.

In the remote-control manipulator system 100 according to Embodiment 1 configured in this way, while the slave arm 1 is performing the manual operation or the hybrid operation, when the operator zooms up or zooms in the camera 3, the display device 6 displays on the display screen 60 the image information currently imaged by the camera 3 and the circumference information which is the information related to the circumference area of the area currently imaged by the camera 3 so that those information are interlocked.

Therefore, the operator is able to grasp the posture of the slave arm 1 or the spatial relationship between the slave arm 1 and the object 16 by looking at the display screen 60 of the display device 6. Thus, it becomes unnecessary to confirm the posture of the slave arm 1 or the spatial relationship between the slave arm 1 and the object 16 by watching the slave arm 1 etc. or frequently changing the zoom of the camera 3 like the conventional remote-control manipulator system, and the work burden is reduced.

Therefore, in the remote-control manipulator system 100 according to Embodiment 1, the operator becomes easier to focus on the remote-controlling work, mistakes of operation are reduced, and fatigue of the worker is reduced. Moreover, the work efficiency of the remote control is improved.

Note that, in Embodiment 1, although a form in which the image information is displayed in the center portion 60A of the display screen 60, and the circumference information is displayed in the circumferential edge portion 60B of the display screen 60 is adopted, the present disclosure is not limited to this configuration. For example, it may adopt a form in which the display screen 60 is divided into two, and the image information is displayed in one side while the circumference information is displayed in the other side. In this case, a ratio of the screens may be 1:1, 2:1, 3:1, 4:1, or 5:1.

Embodiment 2

A remote-control manipulator system according to Embodiment 2 is configured so that, in the remote-control manipulator system according to Embodiment 1, the control device determines whether the slave arm currently manipulated by the operator contacts equipment disposed in the workspace.

Moreover, in the remote-control manipulator system according to Embodiment 2, the control device may be configured to display warning on the display device if it determines that the slave arm currently manipulated by the operator contacts the equipment disposed in the workspace.

Below, one example of the remote-control manipulator system according to Embodiment 2 is described in detail with reference to FIG. 7. Note that, since the remote-control manipulator system 100 according to Embodiment 2 has a similar configuration to the remote-control manipulator system 100 according to Embodiment 1, detailed description of the configuration thereof is omitted.

[Operation and Effect of Remote-Control Manipulator System]

Figure 8:
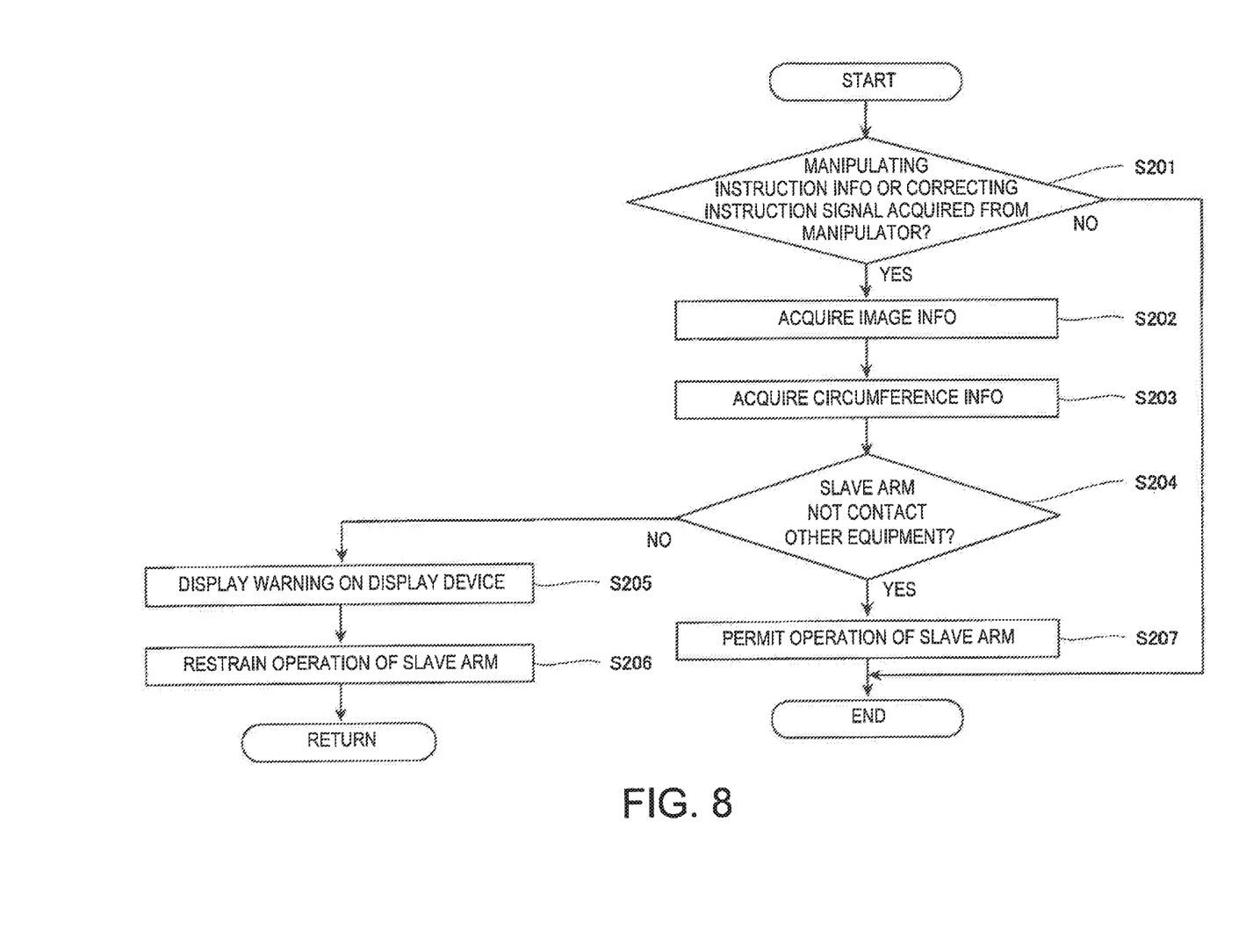
FIG. 8 is a flowchart illustrating operation of a remote-control manipulator system according to Embodiment 2.

FIG. 8 is a flowchart illustrating operation of the remote-control manipulator system according to Embodiment 2. Note that the following operation is executed by the arithmetic part of the control device 4 reading the program stored in the memory part or the storage device 5.

As illustrated in FIG. 8, the control device 4 determines whether the manipulating instruction information or the correcting instruction information is acquired from the manipulator 2 (Step S201). Specifically, the motion controller 43 of the control device 4 determines whether the manipulating instruction information or the correcting instruction information is acquired from the manipulator 2 through the receiver 40.

If the motion controller 43 of the control device 4 determines that the manipulating instruction information or the correcting instruction information is not acquired from the manipulator 2 (No at Step S201), it ends this program. Note that, when the control device 4 ends this program, it again executes this program, for example, after 50 msec.

On the other hand, if the motion controller 43 of the control device 4 determines that the manipulating instruction information or the correcting instruction information is acquired from the manipulator 2 (Yes at Step S201), it executes processing illustrated at Step S202.

At Step S202, the motion controller 43 of the control device 4 acquires the image information currently imaged by the camera 3 through the receiver 40. Subsequently, the motion controller 43 of the control device 4 acquires the circumference information from the posture information acquirer 42 (Step S203).

Next, the motion controller 43 of the control device 4 determines whether the slave arm 1 currently operated by the manipulator 2 does not contact other equipment disposed in the workspace based on the manipulating instruction information or the correcting instruction information acquired at Step S201, the image information acquired at Step S202, and the circumference information acquired at Step S203 (Step S204).

Specifically, the motion controller 43 of the control device 4 determines whether the slave arm 1 currently operated by the manipulator 2 does not contact other equipment based on a distance between the slave arm 1 currently operated by the manipulator 2 and other equipment, a moving direction or a moving speed of the slave arm 1, and if the other equipment is moving, a moving direction or a moving speed of the equipment.

Here, other equipment disposed in the workspace may be, for example, a slave arm 1 adjacent to another slave arm 1 currently operated by the manipulator 2, or may be a workpiece gripped by another slave arm 1, or may be a wall, a pillar, or a ceiling of the factory, or may be apparatus which carries the workpiece, such as the belt conveyor.

If the motion controller 43 of the control device 4 determines that the slave arm 1 currently operated by the manipulator 2 will possibly contact other equipment (No at Step S204), it displays warning on the display device 6 through the output controller 44 (Step S205). Note that the warning may be displayed (outputted) on the display device 6 as text information (image information), such as "A possible contact with other equipment." Moreover, it may be outputted as voice information with a speaker etc., instead of the display device 6.

Next, the motion controller 43 of the control device 4 restrains the operation of the slave arm 1 (Step S206), and it repeats Steps S201 to S206 until it determines that the slave arm 1 does not contact other equipment.

Note that the restraint of the operation of the slave arm 1 may be, for example, operating the slave arm 1 at a small moving speed, or may be prohibiting the operation of the slave arm 1.

On the other hand, if the motion controller 43 of the control device 4 determines that the slave arm 1 currently operated by the manipulator 2 does not contact other equipment disposed in the workspace (Yes at Step S204), it permits the operation of the slave arm 1 (Step S207), and ends this program. Note that the permission of the operation of the slave arm 1 means that the slave arm 1 is operated without the restraint.

In the remote-control manipulator system 100 according to Embodiment 2 configured in this way, since, if the slave arm 1 currently operated by the manipulator 2 will possibly contact other equipment disposed in the workspace, the operation of the slave arm 1 is restrained, an interruption of the work due to a contact with other equipment is reduced.

Embodiment 3

The remote-control manipulator system according to Embodiment 3 is configured so that, in the remote-control manipulator system according to Embodiment 1 or 2, a plurality of slave arms are installed in the workspace, and the control device displays on the display device the posture information on the slave arm adjacent to another slave arm currently manipulated by the operator as the circumference information.

Below, one example of the remote-control manipulator system according to Embodiment 3 is described with reference to FIG. 9.

[Configuration, Operation and Effect of Remote-Control Manipulator System]

Although the remote-control manipulator system 100 according to Embodiment 3 has a similar configuration to the remote-control manipulator system 100 according to Embodiment 1, it differs in the image information and the circumference information which are displayed on the display device 6.

Figure 9:
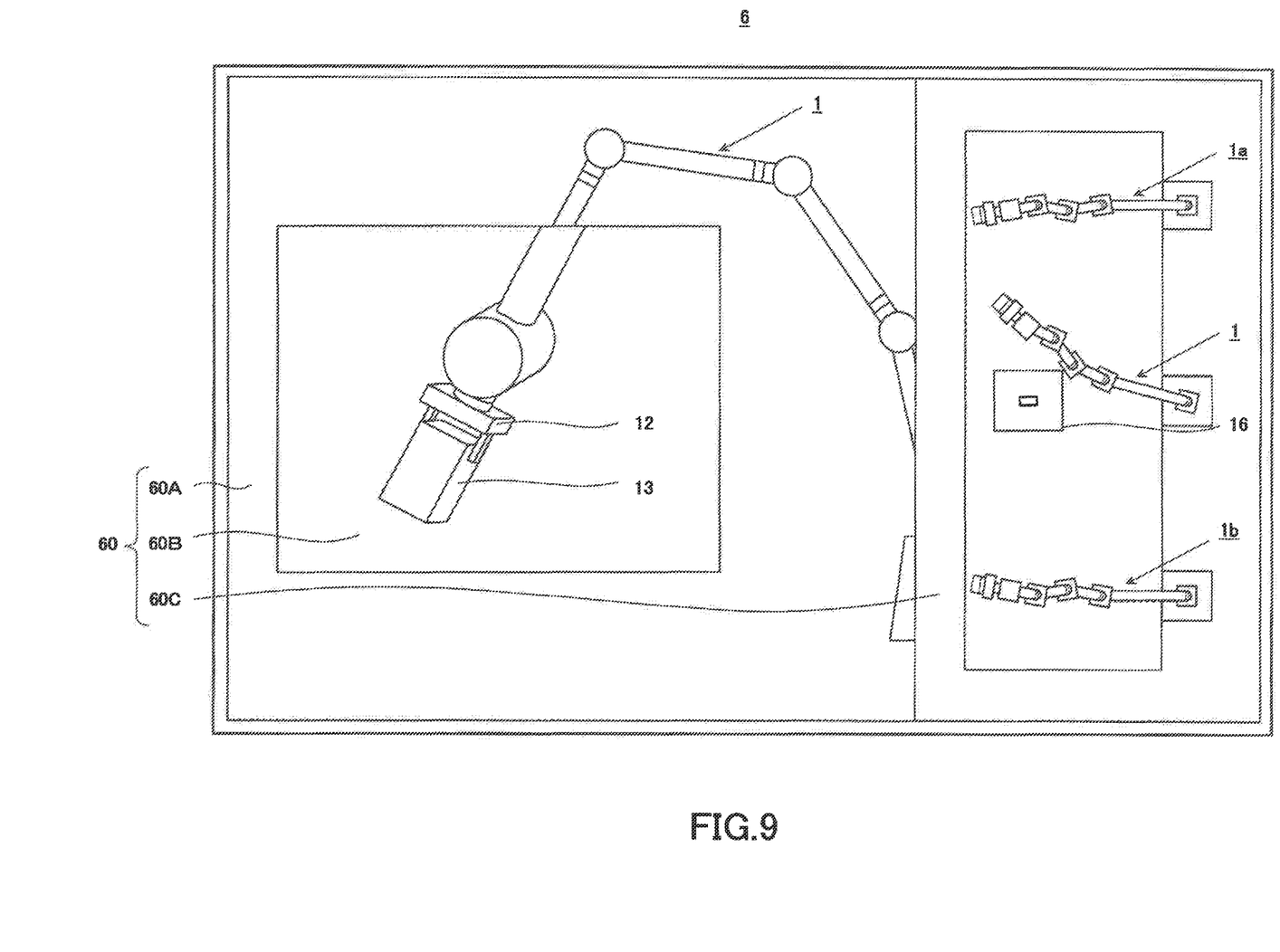
FIG. 9 is a schematic diagram illustrating a display screen of a display device in a remote-control manipulator system according to Embodiment 3.

FIG. 9 is a schematic diagram illustrating a display screen of the display device in the remote-control manipulator system according to Embodiment 3.

As illustrated in FIG. 9, in the remote-control manipulator system 100 according to Embodiment 3, posture information on the slave arms 1A and 1B adjacent to the slave arm 1 currently manipulated by the operator with the manipulator 2 is displayed in a right-side edge portion 60C of the display screen 60 of the display device 6, in addition to the posture information on the slave arm 1 currently operated by the operator with the manipulator 2.

Moreover, in order for the operator to easily understand whether the slave arm 1 will possibly contact the adjacent slave arms 1A and 1B, an image seen from above is displayed in the right-side edge portion 60C.

Even with the remote-control manipulator system 100 according to Embodiment 3 configured in this way, similar operations and effects to those of the remote-control manipulator system 100 according to Embodiments 1 and 2 are obtained.

It is apparent for a person skilled in the art that many improvements or other embodiments of the present disclosure are possible from the above description. Therefore, the above description is to be interpreted only as illustration, and it is provided in order to teach a person skilled in the art the best mode which implements the present disclosure. Details of the structures and/or the functions may be substantially changed without departing from the spirit of the present disclosure.

INDUSTRIAL APPLICABILITY

Since the remote-control manipulator system of the present disclosure and the method of operating the same are capable of reducing the worker's burden and improving the work efficiency, they are useful in the field of industrial robots.

DESCRIPTION OF REFERENCE CHARACTERS

1 Slave Arm
2 Manipulator
3 Camera
4 Control Device
5 Storage Device
6 Display Device 10 Base
11 Base Shaft Part
12 Tip-end Part
13 Target Object
14a Joint Part
14b Joint Part
14c Joint Part
14d Joint Part
14e Joint Part
15a Link Part
15b Link Part
15c Link Part
15d Link Part
16 Object
16a Hole
40 Receiver
41 Circumference Information Acquirer
42 Posture Information Acquirer
43 Motion Controller
44 Output Controller
51 Operation Sequence Information
52 Environment Model
60 Display Screen
60A Center Portion
60B Circumferential Edge Portion
60C Right-side Edge Portion
100 Remote-control Manipulator System

What is claimed is:

1. A remote-control manipulator system, comprising:
a manipulator configured to receive a manipulating instruction from an operator;
a slave arm, installed in a workspace and configured to perform a series of works comprised of a plurality of processes;
a camera configured to image operation of the slave arm;
a display device configured to display an image captured by the camera;
a storage device configured to store information related to environment in the workspace as an environment model; and
a control device,
wherein the control device is configured, while operating the slave arm manually or hybridly, to acquire circumference information that is information related to a circumference area of an area imaged by the camera based on the environment model stored in the storage device, and display on the display device the image captured by the camera and the circumference information in an interlocked state, and the control device acquires the circumference information when the camera is in a zoom-in or zoom-up state, and
a scale of the circumference information displayed on the display device is different from a scale of the image captured by the camera displayed on the display device when displayed in the interlocked state.

2. The remote-control manipulator system of claim 1, wherein the display device is configured to display the image captured by the camera in a center portion and the circumference information in a circumferential edge portion.

3. The remote-control manipulator system of claim 1, wherein the control device is configured to acquire posture information on the slave arm, identify an imaging position of the camera based on the posture information, and identify the circumference information based on the environment model.

4. The remote-control manipulator system of claim 1, wherein the circumference information is an operating area of the slave arm.

5. The remote-control manipulator system of claim 1, wherein,
a plurality of slave arms are installed in the workspace, and
the control device is configured to display on the display device, posture information on a slave arm adjacent to the slave arm currently manipulated by the operator, as the circumference information.

6. The remote-control manipulator system of claim 1, wherein the control device is configured to determine whether the slave arm currently manipulated by the operator contacts equipment disposed in the workspace.

7. The remote-control manipulator system of claim 6, wherein the control device is configured to display warning on the display device when the control device determines that the slave arm currently manipulated by the operator contacts the equipment disposed in the workspace.

8. The remote-control manipulator system of claim 1, wherein the circumference information is displayed entirely outside of the image captured by the camera.

9. The remote-control manipulator system of claim 1, wherein the zoom-in or zoom-up state of the camera causes the slave arm to appear in the captured image closer than an actual distance of the slave arm from a focal plane of the camera.

10. A method of operating a remote-control manipulator system including a manipulator configured to receive a manipulating instruction from an operator, a slave arm installed in a workspace and configured to perform a series of works comprised of a plurality of processes, a camera configured to image operation of the slave arm, a display device configured to display an image captured by the camera, and a storage device configured to store information related to environment in the workspace as an environment model, comprising:
(A) while the slave arm is operated manually or hybridly, identifying circumference information that is information related to a circumference area of an area imaged by the camera based on the environment model stored in the storage device, the identifying being performed when the camera is in a zoom-in or zoom-up state; and
(B) causing the display device to display the image captured by the camera and the circumference information in an interlocked state, wherein
a scale of the circumference information displayed on the display device is different from a scale of the image captured by the camera displayed on the display device when displayed in the interlocked state.

11. The method of claim 10, wherein the display device displays the image captured by the camera in a center portion and the circumference information in a circumferential edge portion.

12. The method of claim 10, wherein the identifying (A) includes identifying an imaging position of the camera based on posture information on the slave arm, and identifying the circumference information based on the environment model.

13. The method of claim 10, wherein the circumference information is an operating area of the slave arm.

14. The method of claim 10, wherein,
a plurality of slave arms are installed in the workspace,
the identifying (A) includes causing the display device to display posture information on a slave arm adjacent to the slave arm currently manipulated by the operator as the circumference information.

15. The method of claim 10, further comprising (C) determining whether the slave arm currently manipulated by the operator contacts equipment disposed in the workspace.

16. The method of claim 15, further comprising, when, in the determining (C), the slave arm currently manipulated by the operator is determined to contact the equipment disposed in the workspace, (D) causing the display device to display warning.

17. The method of claim 10, wherein the circumference information is displayed entirely outside of the image captured by the camera.

18. The method of claim 10, wherein the zoom-in or zoom-up state of the camera causes the slave arm to appear in the captured image closer than an actual distance of the slave arm from a focal plane of the camera.

* * * * *